United States Patent [19]

Saito et al.

[11] Patent Number: 4,984,602
[45] Date of Patent: Jan. 15, 1991

[54] PRESSURE CONTROL APPARATUS AND APPARATUS FOR EFFECTING EXTRACTION CHROMATOGRAPHIC SEPARATION, AND FRACTIONATION BY EMPLOYING THE SAME

[75] Inventors: Muneo Saito, Hachioji; Yoshio Yamauchi, Hino; Hiromi Kashiwazaki, Hachioji; Michiaki Sugawara, Hachioji; Toshinobu Hondo, Hachioji, all of Japan

[73] Assignee: Nihon Bunko Kogyo Kabushiki Kaisha, Tokyo, Japan

[21] Appl. No.: 455,804

[22] Filed: Dec. 22, 1989

Related U.S. Application Data

[62] Division of Ser. No. 143,928, Jan. 14, 1988, abandoned.

[30] Foreign Application Priority Data

Jan. 17, 1987 [JP] Japan ................. 62-008652
Aug. 13, 1987 [JP] Japan ................. 62-202380

[51] Int. Cl.$^5$ .................................... G05D 16/20
[52] U.S. Cl. ...................... 137/487.5; 251/129.05
[58] Field of Search ................ 137/487.5; 251/129.05

[56] References Cited

U.S. PATENT DOCUMENTS

| | | | |
|---|---|---|---|
| 3,074,407 | 4/1987 | Griswold | 251/129.05 X |
| 4,018,241 | 4/1977 | Sodal | 137/487.5 X |
| 4,253,480 | 3/1981 | Kessel | 137/487.5 X |
| 4,373,697 | 2/1983 | Phelps | 251/129.05 |
| 4,597,943 | 7/1986 | Sugiyama et al. | |
| 4,641,623 | 2/1987 | Murner | 137/487.5 |
| 4,669,660 | 6/1987 | Weber | 251/129.05 X |
| 4,766,921 | 8/1988 | Williams | 251/129.05 X |

FOREIGN PATENT DOCUMENTS 0016666 10/1980 European Pat. Off. .
0102528 3/1984 European Pat. Off. .

OTHER PUBLICATIONS

New Double-Stage Separation Analysis Method, Chromsymp. 622, *Journal of Chromatography*, 332 (1985), 107–116, Elsevier Science Publishers B.V., Amsterdam-printed in The Netherlands.

Integral Pressure Restrictor for Capillary SFC, E. J. Guthrie, *Journal of Chromatographic Science*, vol. 24, Jun. 1986.

*Primary Examiner*—Alan Cohan
*Attorney, Agent, or Firm*—Browdy and Neimark

[57] ABSTRACT

A pressure control apparatus is used in an apparatus for effecting extraction, chromatographic separation, and fractionation. The pressure control apparatus is intended to reduce the amount of a fluid stagnating in a valve, and is arranged to cyclically open and close the valve, thereby controlling the level of pressure. An apparatus for effecting extraction, chromatographic separation, and fractionation is designed to perform in an on-line manner the extraction of soluble components contained in a sample as well as the separation and fractionation of the components. A chromatography is connected to a downstream side of a supercritical fluid extraction device, and the aforesaid pressure control apparatus is used as back-pressure regulators (9, 18) for the chromatography and the extraction device. An extraction fluid and an elution fluid which are used in a mobile phase may be a common fluid (FIG. 1) or separate fluids (FIG. 10). At the time of extraction, the soluble components of the sample within an extraction vessel (6) is extracted by a supercritical fluid, and is delivered to an adsorption column (14). The supercritical fluid is converted into a gas by reducing the pressure within the adsorption column and thus the solubility of the fluid is lowered so that the resultant extract is adsorbed by an adsorbent packed in this column. At the time of chromatographic separation, the pressure within the adsorption column (14) is maintained at a critical pressure or higher and thus an extract is eluted by the supercritical fluid and is delivered to a separation column (16), in which the extract is separated into individual components. Then, when the pressure within the adsorption column is reduced, the supercritical fluid is gasified and the result components are collected as fractions.

8 Claims, 9 Drawing Sheets

PRESSURE CONTROL APPARATUS AND APPARATUS FOR EFFECTING EXTRACTION CHROMATOGRAPHIC SEPARATION, AND FRACTIONATION BY EMPLOYING THE SAME

This is a division of Ser. No. 143,928, filed Jan. 14, 1988, now abandoned.

BACKGROUND OF INVENTION

1. Field of the Invention

The present invention relates to a pressure control apparatus for providing control over the fluid pressure of a gas or a liquid within a container or a flow passage, and to an apparatus employing the same, that is, an apparatus for effecting extraction, chromatographic separation and, fractionation which apparatus is arranged to extract a soluble substance from a sample by the use of a supercritical fluid or a liquefied gas, introduce the resultant extract into a chromatograph in an on-line manner for separation into individual components, and collect them as fractions.

2. Description of the Prior Art

The present inventor proposed an extraction/-chromatographic separation apparatus capable of extracting a soluble substance from a sample by using a supercritical fluid or a liquefied gas and introducing the resultant extract into a chromatograph in an on-line manner, thereby separating the individual components of that extract (Journal of Chromatography, 332 (1985), pages 107 to 116).

The aforementioned extraction/chromatographic separation apparatus is arranged to deliver an extraction/elution fluid containing the supercritical fluid or the liquefied gas by means of a pump to the interior of an extraction vessel including a sample, extract a soluble component from the sample in the extraction vessel, cause the extract primarily obtained in a flow passage downstream of the extraction vessel to be drawn at a low pressure into a trapping loop previously charged with the extraction/elution fluid in the gaseous phase thereof, temporarily store that extract in that trapping loop, and introduce the extract to the chromatograph in an on-line manner.

A back pressure control valve for allowing the extract to be separated into its individual components in a separation column and for introducing the resultant components into a detector is disposed downstream of the detector which constitutes a part of the chromatograph.

The above-described apparatus accomplishes a substantial improvement in that extraction and separation can be effected in an on-line manner.

However, it is necessary to set the trapping loop apart from the extraction vessel and the separation column of the chromatograph, to connect the trapping loop to only one of the extraction vessel and the separation column, or to connect the trapping loop directly to the pump. Therefore, three six-way valves are needed, and this necessity disadvantageously complicates the construction and operation of the apparatus.

In general, typical prior art pressure control apparatus have been arranged to provide control so that a detection pressure may be set to a desired pressure by adjustment of spring force which is loaded on the pressure sensing piston, on which a value needle is installed so as to change the opening of a pressure control valve. Such a valve is commercially available from Tescom (MN).

However, since this pressure control valve is arranged to adjust the opening of the gap between a valve seat and a needle member by the movement of the pressure sensing piston, the volumes of the spaces defined upstream and downstream of that gap are relatively large and therefore the amount of fluid stagnating in the valve may reach at least several to several tens of milliliters.

As a result, even if separation is complete in the separation column, for example, in the previously-mentioned supercritical fluid chromatograph, an effluent may flow from the column into the pressure control valve to cause re-mixture of the separated components.

To the end of preventing such re-mixture, in a supercritical fluid chromatograph of the type employing a capillary column, a capillary tube having an inner diameter of 10 m or less is connected to a downstream side of the separation column so that the flow resistance of the supercritical fluid is utilized to maintain a required level of fluid pressure (Journal of Chromatographic Science, Vol. June 14, 1986, pages 236 to 241).

However, in order to vary the level of pressure, the flow rate of the fluid in the mobile phase must also be varied, with the result that the pressure and the flow rate both of which determine the period of retention time are varied at the same time. Therefore, it has been impossible to examine the details of the characteristics of the retention time by independently varying only one of the pressure and the flow rate.

It is known that a method of effecting separation under reduced pressure is widely used in supercritical fluid extraction apparatus. In this method, the level of pressure is lowered to cause a reduction in the solubility of an extract in the supercritical fluid, thereby separating and collecting a desired solute from the fluid.

However, if the aforesaid pressure control valve arranged to adjust the valve opening is used in a small supercritical fluid extraction apparatus, the following problems are encountered. Since a large amount of fluid stagnates in the pressure control valve, individual separated extracts are re-mixed within the pressure control valve, and this makes it impossible to fractionate the individual extracted substances. In addition, since the extracts stagnate in the valve when the pressure of the fluid, i.e., extraction medium, decreases rapidly causing solubility reduction, they are easily precipitated and adhered onto inner walls of the valve, thereby hindering the extracted substances from being completely fractionated. In addition, such precipitated substances often block the flow path of the valve.

SUMMARY OF THE INVENTION

It is therefore an object of the present invention to provide a pressure control apparatus in which the amount of a fluid stagnating in a valve thereof is reduced.

It is another object of the present invention to provide an apparatus capable of effecting extraction and chromatographic separation as well as fractionation by means of a simple construction and in an on-line manner.

It is still another object of the present invention to provide an apparatus for effecting extraction, chromatographic separation, and fractionation in which apparatus the individual components of an extract separated in a separation column can be fractionated by independently controlling the flow rate and pressure of a fluid in the mobile phase.

To the end of achieving the above and other objects, in accordance with a first aspect of the present invention, there is provided a pressure control apparatus in which the amount of a fluid stagnating upstream and downstream of the portion opened and closed by a valve can be minimized since the apparatus employs a valve electrically operated to open and close the flow passage between an inlet of the valve and its outlet without mechanical pressure sensing piston. Since the valve is arranged to be periodically opened and closed in a short period of time, the mean value of the time period during which the fluid stagnates in the portion opened and closed by the valve is extremely small so that it is possible to further reduce the substantial amount of the fluid stagnating in the valve. In addition, since the valve is periodically opened and closed and since the amount of the fluid stagnating in the valve is extremely small, substances contained in the fluid do not easily adhere to inner walls of the valve. Moreover, since the valve is always in either fully opened state or fully closed state, the speed of response of the valve is high. Since the periodic opening and closing motions of the valve are rapidly performed, the amplitude of variations in pressure is relatively small so that accurate pressure control can be provided.

In accordance with a second aspect of the present invention, there is provided an apparatus for effecting extraction, chromatographic separation, and fractionation. In this apparatus, a chromatograph is connected to a downstream side of an extraction device, back pressure regulating means is provided for generating back pressures required for extraction in the extraction device and for chromatographic separation in the chromatograph, and an adsorption column packed with an adsorbent acting to adsorb extracts is disposed between the back pressure regulating means of the extraction device and a separation column of the chromatograph. Accordingly, extraction and separation can be effected in an on-line manner by means of a simple construction and by a simple operation.

In addition, the aforesaid apparatus produces an excellent effect in that it is possible to independently control the flow rate and pressure of the fluid in the mobile phase and also to fractionate the individual components of extracts which are separated and flow out of the separation column.

In accordance with a third aspect of the present invention, there is provided another form of apparatus for effecting extraction, chromatographic separation, and fractionation. In addition to the arrangement according to the second aspect, this apparatus further includes a pump for delivering an extraction fluid and a pump for delivering an elution fluid, these pumps being disposed separately from each other. At the time of extraction, the former pump is actuated to cause the extraction fluid to flow from the back pressure control means of the extraction device to the adsorption device. At the time of chromatographic separation, the latter pump is actuated to cause the elution fluid to flow into the adsorption column. Accordingly, in addition to the effects accomplished by the hereinbefore described apparatus according to the second aspect, extraction and cleaning of the chromatograph can be performed at the same time and it is therefore possible to greatly reduce the time period required for the entire processing.

Moreover, since the extraction fluid is separated from the elution fluid, optimum separation can be achieved prior to the steps of chromatographic separation and fractionation without the need to replace the elution fluid.

DESCRIPTION OF THE PREFERRED EMBODIMENTS

A preferred embodiment of the present invention will be described below with reference to the accompanying drawings.

Figure 1:
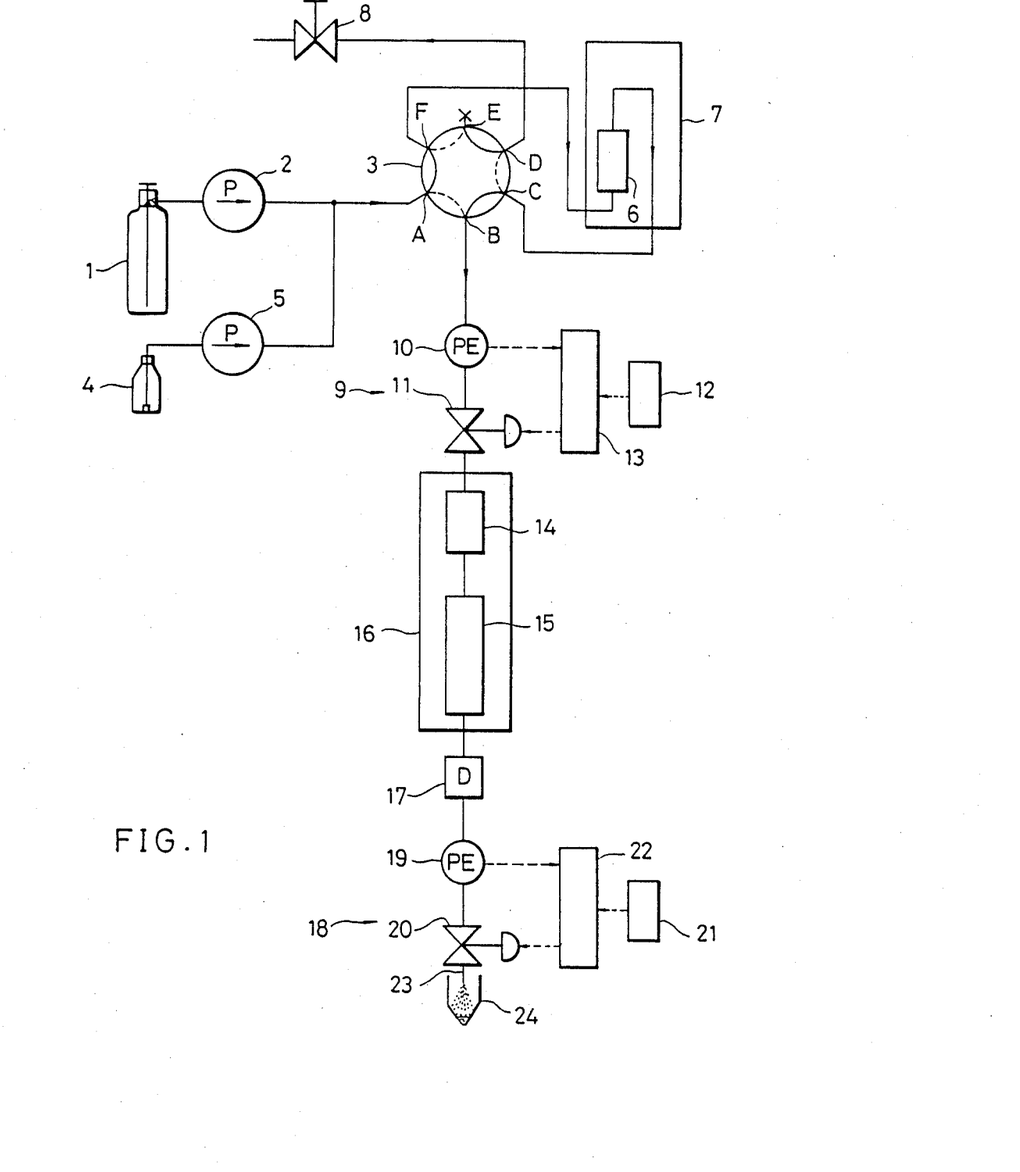
FIG. 1 is a circuit diagram illustrating an apparatus for effecting extraction, chromatographic separation, and fractionation in accordance with one embodiment of the present invention.

FIG. 1 illustrates in block form an apparatus for effecting extraction, chromatographic separation, and fractionation, which apparatus incorporates a preferred embodiment of the present invention.

A cylinder 1 contains a liquefied gas which is used as an extraction/elution fluid for extraction and chromatographic separation.

The outlet of the cylinder 1 is connected to the inlet of a pump 2, and the outlet of the pump 2 in turn is connected to a port A of a six-way valve 3. The pump 2 is cooled by a cooling unit (not shown). A storage tank 4 stores therein a modifier solvent which constitutes a part of the extraction/elution fluid. The outlet of the storage tank 4 is connected to the inlet of the pump 5, and the outlet of the pump 5 is connected to a pipe which interconnects the pump 2 and the six-way valve 3.

The six-way valve 3 can be switched-over between two positions, that is, a position at which flow passages B-C, D-E and F-A (shown by solid lines) are opened, while flow passages A-B, C-D and E-F (shown by dashed lines) are closed, and a position at which, conversely, the former flow passages are closed with the latter flow passages being opened.

A port F of the six-way valve 3 is connected to the inlet of an extraction vessel 6, and the outlet of the extraction vessel 6 is connected to a port C of the six-way valve 3. The extraction vessel 6 contains therein a sample, which may be either a liquid or a solid. If a liquid sample is employed, it is preferably absorbed into a liquid absorptive substance in order to extend the contact area with the fluid and, in this absorbed form, is accommodated in the extraction vessel 6. In this fashion, a desired extract alone is eluted and flows out of the extraction vessel 6. The extraction vessel 6 is housed in a thermostatic chamber 7 whose internal temperature is adjustable.

In this state, a port E of the six-way valve 3 is closed and a port D of the six-way valve 3 communicates with the atmosphere through a valve 8.

A port B of the six-way valve 3 is connected to the inlet of a back pressure regulator indicated generally at 9. The back pressure regulator 9 includes a pressure transducer 10 for detecting a back pressure, a pressure control valve 11 having an adjustable valve opening, a pressure setting device 12, and a pressure adjusting device 13 for controlling the valve opening so as to adjust a back pressure to the set pressure. It is preferable to employ the pressure control valve 11 having a small internal volume in order to prevent the extract from stagnating or trapped within the same.

The outlet of the back pressure regulator 9, that is, the outlet of the pressure control valve 11 is connected to the inlet of an adsorption column 14. The adsorption column 14 is packed with an adsorbent acting to adsorb the substances extracted from the sample when the solubility of the extract in the fluid thereof is low. The outlet of the adsorption column 14 is connected to the inlet of a separation column 15 packed with a material supporting stationary phase. In a similar manner to that of the extraction vessel 6, the adsorption column 14 and the separation column 15 are housed in a thermostatic chamber 16 whose internal temperature is adjustable.

The outlet of the separation column 15 is connected to the inlet of a back pressure regulator indicated generally at 18 through a detector 17 used to monitor the effluent. The back pressure regulator 18, which has the same arrangement as the back pressure regulator 9, includes a pressure transducer 19, a pressure control valve 20, a pressure setting device 21, and a pressure adjusting device 22.

An outlet pipe 23 is connected to an outlet port of the pressure control valve 20, and a collection reservoir 24 for fractionation of extracts is disposed at a position below the outlet pipe 23.

The following is a description of this embodiment having the aforesaid arrangement.

As necessity demands, the following flow-passage cleaning operation is carried out as a preparatory step.

First, the flow passages A-B, C-D and E-F of the six-way valve 3, which are illustrated by the dashed lines, are opened and the set pressure (or gauge pressure) of the back pressure regulator 9 is set to zero, that is, the pressure control valve 11 is fully opened.

In a case where a supercritical fluid is employed for the flow-passage cleaning operation, the set pressure of the back pressure regulator 18 is raised to a desired pressure, and the temperature within the thermostatic chamber 16 is raised to a desired temperature. The pressure and temperature are set to predetermined values which correspond to the solubility characteristics of a substance to be removed by cleaning. In this state, the pumps 2 and 5 are actuated to deliver the liquefied gas from the cylinder 1 and the modifier solvent from the storage tank 4. Within the adsorption column 14 and the separation column 15, the liquefied gas serves as a supercritical fluid having a relatively greater degree of solubility than that of a gas. The temperature and pressure conditions within the separation column 15 are substantially the same as those in the flow passage between the separation column 15 and the pressure control valve 20 and those in a somewhat upstream side of the adsorption column 14. Accordingly, the supercritical fluid having a relative great degree of solubility is allowed to flow through these flow passages. The modifier solvent acts to increase the solubility of the supercritical fluid in the mobile phase. In consequence, the solubility in the mobile phase is increased to perform the effective cleaning of the flow passages.

Then, the following extraction as will be described later is performed.

A sample is placed in the extraction vessel 6.

When extraction is to be conducted using the supercritical liquid, the temperature within the thermostatic chamber 7 is raised to a critical temperature or higher, the pressure of the back pressure regulator 9 is raised to a critical pressure or higher, and the set pressure of the back pressure regulator 18 is set to zero, that is, the pressure control valve 20 is fully opened. The six-way valve 3 is switched to open the solid-line flow passages B-C, D-E and F-A.

In this manner, the liquefied gas within the cylinder 1 and the modifier solvent in the storage tank 4 are delivered to the extraction vessel 6, and the liquefied gas is converted into a supercritical fluid therein. Thus, soluble components are extracted from the sample placed in the extraction vessel 6 in correspondence with the temperature and pressure within the same, and the resultant extract, flowing out of the extraction vessel 6, passes through the back pressure regulator 9. Since the pressure control valve 20 is fully opened, the supercritical fluid, after leaving the pressure control valve 11, is gasified by its rapid pressure drop and enters the adsorption column 14. Accordingly, since the solubility of the extract in the mobile phase rapidly lowers, the extract is precipitated and adsorbed onto the adsorbent packed in the adsorption column 14 and therefore hardly flows into the separation column 15, that is, all part of the extract is trapped within the adsorption column 14.

After completion of the aforesaid extraction, the following separation and fractionation are performed.

In a case where separation and fractionation are to be conducted with the supercritical fluid, the temperature within the thermostatic chamber 16 is raised to a critical temperature or higher, and the pressure setting device 12 is operated to adjust a set pressure to a zero level, that is, the pressure control valve 11 is fully opened and the back pressure regulator 18 is set to the critical pressure or higher. In this state, the valve 8 is opened, and the six-way valve 3 is switched to open the dashed-line flow passages A-B, C-D and E-F.

In this manner, the liquefied gas within the cylinder 1 and the modifier solvent within the storage tank 4 are delivered to the adsorption column 14. The liquefied gas is converted into a supercritical fluid having a relatively great degree of solubility with respect to the extract to cause desorption of the extract adsorbed onto the adsorbent packed in the adsorption column 14, and the extract is introduced into the separation column 15. The extract is then subjected to chromatographic separation in the separation column 15, and then the column effluent is passed through the detector 11 and the back pressure regulator 18. At this time, the supercritical fluid is gasified by its rapid pressure drop and the effluent is discharged from the outlet pipe 23 as a gas. An operator fractionates the chromatographic peak of interest into collection reservoir 24 at real time in accordance with the detection data supplied by the detector 17. On completion of extraction, the fluid within the extraction vessel 6 is discharged into the atmosphere through the valve 8 as a gas.

It is to be noted that the liquefied gas may be used to perform the aforesaid cleaning, extraction, chromatographic separation, or fractionation. In this case, the temperature and pressure conditions only differ from those of the aforesaid case in which the supercritical fluid is used, and the other conditions are the same. In this case, the temperature is raised to a critical temperature or higher, and the pressure is raised to a predetermined level or higher in correspondence with this temperature. Thus, the liquid is maintained in its mobile phase.

Since this embodiment employs only one six-way valve, the construction and operation are extremely simplified as compared with those of the prior art. In addition, the flow rate and pressure of the fluid in the mobile phase can be independently controlled by means of the pumps 2 and 5 and the back pressure regulators 9 and 18, respectively. It is accordingly possible to obtain the detailed characteristics of retention time by varying only one of the pressure or the flow rate.

The following is a description of one example of fractionation which was performed by using the above-described first embodiment of the apparatus of the present invention.

Wheat germ was used as a sample, a liquefied $CO_2$ gas charged in the cylinder 1 as an extraction/elution fluid, and ethanol as a modifier solvent to be charged in the storage tank 4.

5 g of wheat germ was placed in the extraction vessel 6 having an internal volume of 10 ml, the temperature within the thermostatic chamber 7 was maintained at 40° C., and the level of set pressure is adjusted to 250 kg/cm² by means of the back pressure regulator 9. The liquified $CO_2$ gas was delivered at a rate of 8 ml/min as a liquid at 5° C. and ethanol was delivered at a rate of 0.2 ml/min, and, in this state, extraction was continued for one hour. The adsorption column 14 was a cylindrical container having an internal diameter of 7.2 mm and a length of 50 mm, and porous silica gel having a particle diameter of 30 to 50 μm was packed as an adsorbent into the adsorption column 14.

The separation column 15 was a cylindrical container having an internal diameter of 10.2 mm and a length of 250 mm, and the same silica gel was charged into the aforesaid separation column 15. The detector 17 was a multiwavelength UV detector. The pressure control valves 11 and 20 were each constituted by a solenoid valve 20A having an internal volume of 10 ml. The solenoid valve 20A will be described in detail later in connection with FIG. 5. The pressure adjusting device 13 and 22 were each constituted by a pressure adjusting devices 22A, which will be described in detail below in connection with FIG. 6.

Figure 2:
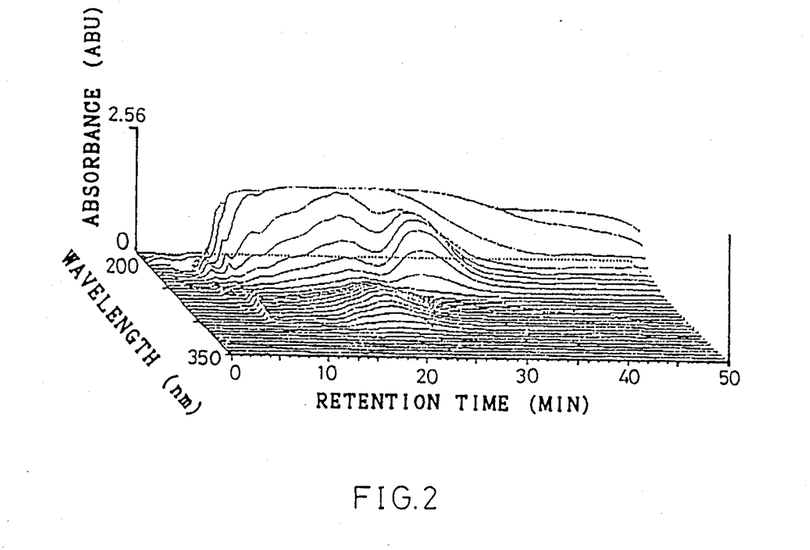
FIG. 2 is a three-dimensional chromatogram obtained by a multiwavelength UV detector when wheat germ is used as a sample in the apparatus shown in FIG. 1.

FIG. 2 shows a three-dimensional chromatogram obtained by the multiwavelength UV detector. The vertical or so-called Z axis represents an absorbance (ABU), the horizontal or X axis representing a wavelength (nm), and the other horizontal or Y axis representing retention time.

Figure 3:
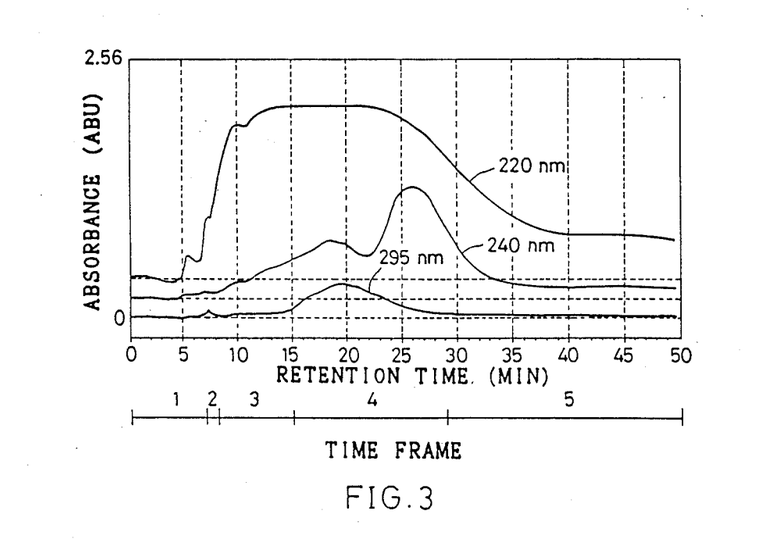
FIG. 3 is a two-dimensional chromatogram which corresponds to wavelengths of 220, 240, and 295 nm in FIG. 2.

FIG. 3 shows the chromatograms which correspond to wavelengths of 220, 240, and 295 nm in FIG. 2.

The chromatogram corresponding to the wavelength of 295 nm represents the elution of tocopherol (vitamin E), and the component was fractionated through the outlet pipe 23 in accordance with the time frames 1 to 5 shown along the horizontal axis (time axis) of FIG. 3 while monitoring that chromatogram at real time.

Figure 4:
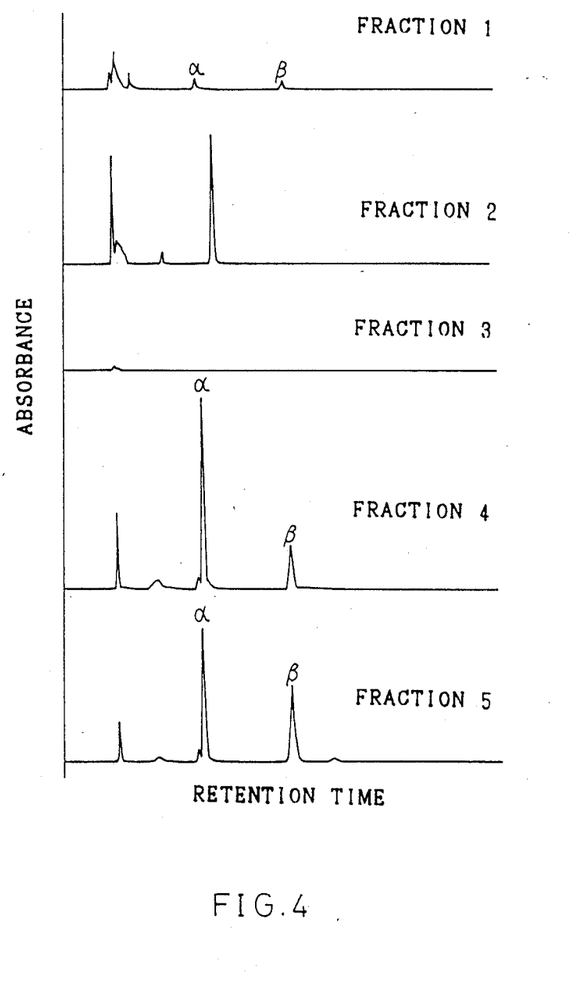
FIG. 4 is a chromatogram obtained by analyzing fractions collected in accordance with the time frames shown in FIG. 3 by means of a high-performance liquid chromatograph.

Respective fractions 1 to 5 corresponding to the time frames 1 to 5 were introduced as samples into a high-performance liquid chromatograph (HPLC), and the chromatograms shown in FIG. 4 were obtained.

In FIG. 4, α represents the chromatographic peaks of α-tocopherols, and α represents the chromatographic peaks of β-tocopherols.

As was expected, fractions 1 and 2 contained only small amounts of tocopherols, whereas fractions 4 and 5 contained significant amounts of tocopherols.

The following table lists the weights of solutes, α-tocopherols and β-tocopherols contained in the respective fractions 1 to 5.

TABLE

| Fraction | Solute (mg) | α-tocopherol (μg) | β-tocopherol (μg) |
|---|---|---|---|
| 1 | 1.1 | 0.3 | 0.3 |
| 2 | 1.9 | 0.1 | — |
| 3 | 82.5 | — | — |
| 4 | 115.4 | 480.0 | 100.0 |
| 5 | 11.3 | 68.8 | 68.8 |
| Total | 212.2 | 549.2 | 169.1 |

Immediately after extraction was completed, a reduction in weight in the extraction vessel 6 and an increase in weight in the adsorption column 14 were measured. The results were both 220 mg. This amount of the extract was entirely used in chromatographic analysis.

The total weight of the solute recovered was 212.2 mg as shown in Table, that is, the total recovery was 96.52% which was an excellent value in fractionation. In this manner, in accordance with the present invention, fractionation using a back pressure regulator was accomplished which had heretofore been impossible of attain.

The following is a description of a typical example of the back pressure regulator 18.

Figure 5:
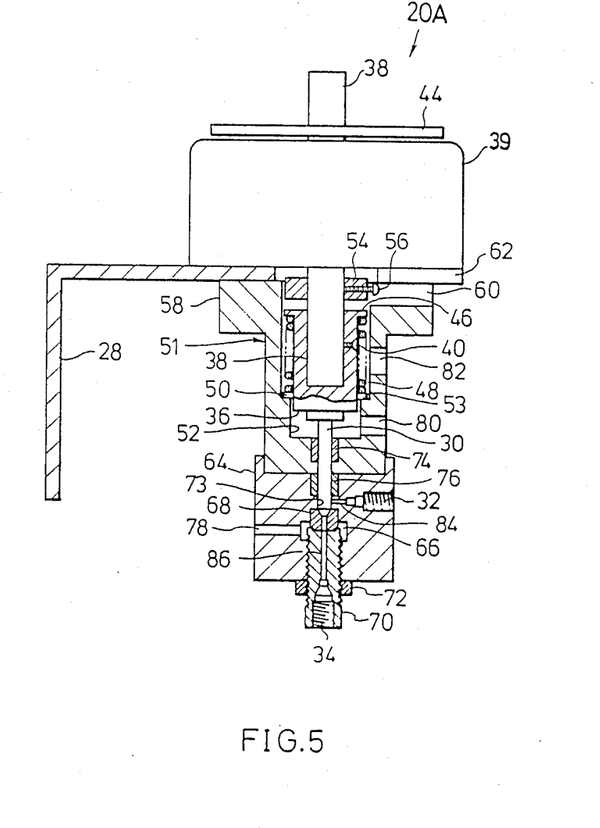
FIG. 5 is a partial, longitudinal section of a solenoid valve which is one constituent element of a pressure control apparatus according to another embodiment of the present invention.

First of all, one example of the construction of the pressure control valve 20 will be described with reference to FIG. 5. The pressure control valve 20 is constituted by a solenoid valve 20A.

The solenoid valve 20A is fixed to a bracket 28, and a valve stem 30 is adapted to move back and forth along the axis thereof, thereby fully opening or closing the flow passage between the inlet 32 and the outlet 34.

A coupling 36 is formed at the proximal end of the valve stem 30, and the proximal end of a plunger 38 is fitted into the coupling 36. The coupling 36 and the plunger 38 are coupled together by a screw 40 which is screwed into a hole formed in the peripheral wall of the coupling 36. The plunger 38 extends through the center of a solenoid 39 enclosed by a cover member. When the solenoid 39 is energized, an iron sheet 44 fixed to an upper end portion (as viewed in FIG. 5) of the plunger 38 is magnetically attracted by the solenoid 39 to cause the plunger 38, the iron sheet 44, and the valve stem 30 to integrally move downwardly as viewed in the same Figure. A flange portion 46 is formed at an upper end (as viewed in FIG. 5) of the coupling 36. A return spring 48 is fitted onto the coupling 36 and a spring support 50 in turn is fitted onto the coupling 36. Thus the return spring 48 is interposed between the flange portion 46 and the spring support 50. The coupling 36 is inserted into a hole 52 which is bored in the axial portion of a housing 51, and the spring support 50 is pressed into engagement with a step 53 formed on the upper end (as viewed in FIG. 5) of the hole 52. A stop ring 54 is fitted onto the portion of the plunger 38 which is defined between the solenoid 39 and the coupling 36. The stop ring 54 is fixed with respect to the plunger 38 by a screw 56 screwed into a hole formed in the periphery of the stop ring 54. When the solenoid 39 is deenergized, the stop ring 54 is pressed into contact with the solenoid 39 by the return motion of the return spring 48. Accordingly, the overall stroke length of the valve stem 30 is determined by a position at which the stop ring 54 is mounted.

A flange 58 is formed at the proximal end of the housing 51 and the bracket 28 is clamped between the flange 58 and the solenoid 39, and cutouts 60 and 62 are formed in the flange 58 and the bracket 28, respectively. Therefore, the point of a screwdriver can be inserted into the cutouts 60 and 62 to rotate the screw 56, thereby enabling adjustment of the mounting position of the stop ring 54.

The proximal end of a body 64 is screwed onto the lower end portion (as viewed in FIG. 5) of the housing 51. A hole 66 is formed in an upper end portion (as viewed in the same Figure) of the body 64, and a valve seat 68 having a sealing function is fitted into the hole 66. A nut 72 is screwed onto a nipple 70 which in turn is screwed into the hole 66, and the nipple 70 is fastened to the body 64 by the nut 72. The valve stem 30 is inserted into a hole 73 which provides communication between the holes 52 and 66. A bushing 74 is fitted into the gap between the valve stem 30 and the housing 51, and a seal ring 76 is fitted into the gap between the valve stem 30 and the body 64. These bushing and seal 74 and 76 may be formed of, for example, a reinforced ethylene tetrafluoride resin, and the valve seat 68 may be formed of, for example, a polyimide resin. In order to cope with the breakage of the valve seat 68, a vent hole 78 is bored in the body 64 for providing communication between the hole 66 and the exterior. Also, in order to cope with the breakage of the cylindrical bushing 74 and seal 76, vent holes 80 and 82 are bored in the housing 51 for provision of communication between the hole 52 and the exterior.

In the aforesaid construction and arrangement, when the solenoid 39 is deenergized, the valve stem 30 is moved upwardly by the resilient force of the return spring 48 to fully open the flow passage between the inlet 32 and the outlet 34. On the other hand, when the solenoid 39 is energized, the valve stem 30 is moved downwardly against the resilient force of the return spring 48 to bring the lower end surface of the valve stem 30 into contact with the valve seat 68, thereby fully closing the flow passage between the inlet 32 and the outlet 34.

The internal diameter of a flow passage 84 for providing communication between the hole 73 and the inlet 32 as well as the internal diameter of a flow passage 86 for providing communication between the hole 73 and the outlet 34 are substantially equal to the internal diameter of a pipe which is connected to the solenoid valve 20A. In addition, since the solenoid 39 is periodically turned on and off, the mean value of the periods during which the fluid stagnates in the hole 73 formed for communication between the flow passages 84 and 86 is extremely small. Accordingly, the amount of the fluid stagnating within the valve is extremely small so that the extract is prevented from being re-mixed within the valve.

In addition, since the valve stem 30 is continuously moved reciprocally, the extract hardly adheres to the inner walls of the valve.

Figure 6:
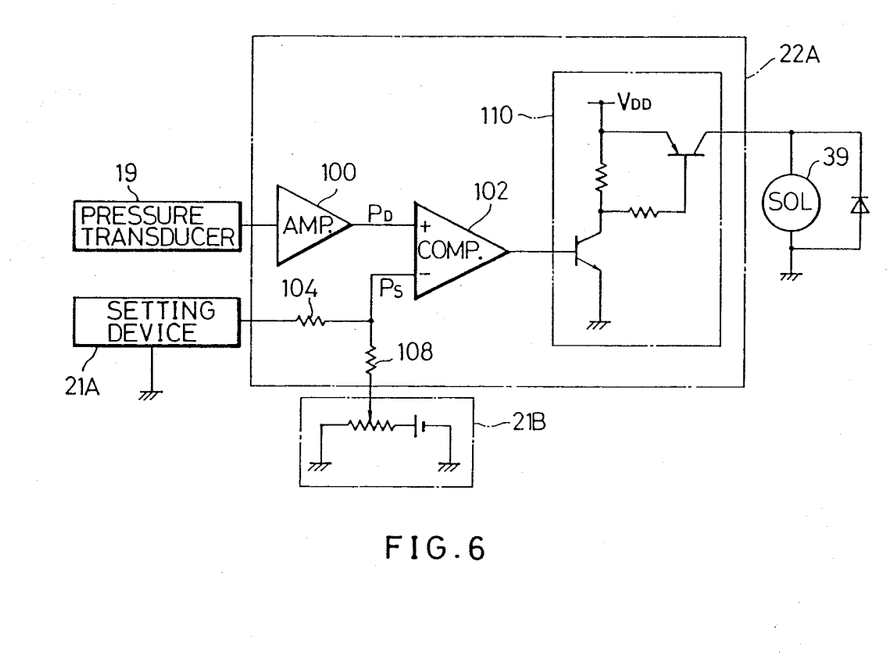
FIG. 6 is a circuit diagram of a pressure adjusting device which is another constituent element of the pressure control apparatus.

One example of the pressure adjusting device 22 will be described below with reference to FIG. 6 in which the example is indicated generally at 22A.

The output voltage of the pressure transducer 19 is supplied to an inverting input terminal of a comparator 102 through an amplifier 100. The output voltage of a programmed setting device 21A is supplied to a non-inverting input terminal of the comparator 102 through a resistor 104. The output voltage of a manual setting device 21B is supplied to this non-inverting input terminal through the resistor 108.

A switch circuit 110 is turned on and off in response to the output voltage of the comparator 102. Only when the output voltage of the comparator 102 goes to a high level, the solenoid 39 is energized. In FIG. 6, a drive voltage is represented by $V_{DD}$.

In the aforesaid construction, in a manual setting mode, the output voltage of the programmed setting device 21A is set to zero, and the variable resistor of the manual setting device 21B is adjusted to set the level of pressure to a desired value. In an automatic setting mode, the output voltage of the manual setting device 21B is set to zero, and the programmed setting device 21A is caused to output a voltage which corresponds to a desired pressure.

If a detection pressure $P_D$ is lower than a set pressure $P_S$, the output voltage of the comparator 102 goes to a high level and the solenoid 39 is energized to fully close the solenoid valve 20A. Thus, when the pressure at the end of the separation column 15 rises to make the detection pressure $P_D$ higher than the set pressure $P_S$, the output voltage of the comparator 102 goes to a low level and the solenoid 39 is deenergized to fully open the solenoid valve 20, thereby reducing the pressure at the end of the separation column 15. When the detection pressure $P_D$ is made lower than the set pressure $P_S$, the above-described operation is repeated and thus the solenoid valve 20A is periodically opened and closed continuously. In other words, the present inventive pressure controlling apparatus constitutes a self-excited oscillator.

The frequency of the aforesaid opening and closing cycle is automatically determined by the set pressure $P_S$, the compressibility of the fluid, the discharges of the respective fluids from the pumps 2 and 5, the flow rate of the fluid passing through the solenoid valve 20A, the elastic coefficient of the container of the separation column 15, and the equivalent capacitance, inductance and resistance of the entire system, as analogous to the electrical system, which are determined by the inductance of the solenoid 39 and the speed of the response of the valve during its opening and closing operations together with the above parameters.

The present inventor produced a solenoid valve including the valve stem 30 having a diameter of 3.2 mm and a stroke length of 1.2 mm and a valve portion having a fluid hold-up volume of about 10 μl. The discharge of the pump 2 was set to 1 to 10 ml/min and the motion of the pump 5 was stopped. In this state, liquefied carbon dioxide was delivered by pressure to the separation column 15 having a volume of 1 to 50 ml, and the temperature of the separation column 15 was raised to a temperature equal to or higher than the critical temperature of carbon dioxide (31.3° C.) to thereby obtain supercritical carbon dioxide. The level of pressure was controlled within a range of 100 to 300 kg/cm$^2$. The frequency of self-excited oscillation, that is, the frequency of the opening and closing motions of the valve automatically varied in correspondence with the discharge of the pump 2 and the level of the set pressure, within a range of about 1 to about 20 Hz. This frequency can also be varied by adjusting the mounting position of the stop ring 54.

In the present apparatus, the accuracy of pressure control is extremely high. For example, the amplitude of pressure variations based on the opening and closing motions of the valve with respect to the set pressure was sufficiently small as compared with the pulsation generated by the pump 2 so that such variations could not be recorded by a pen recorder having a horizontal scale of 20 kg/cm.

It will be appreciated that the aforesaid frequency range is well suited for use in supercritical fluid extraction and supercritical fluid chromatography. This is because, if the detector 17 is constituted by an optical detector or a flame ionization detector, the aforesaid frequencies are not so low as to generate a high level of noise which may hinder the normal detecting operation of the detector 17 (the hydrogen ionization detector is disposed downstream of the solenoid valve 20A).

With the above-described back pressure regulator, it is possible to realize a small amount of stagnant fluid which is equivalent to about 0.001 to about 0.01 percent of the amount of a fluid which stagnates in a pressure adjusting valve constituted by a conventional mechanical servo type of pressure regulator having an adjustable valve opening or by a combination of such a conventional type of pressure adjusting valve and hydraulic and pneumatic servo circuitry.

Accordingly, it becomes possible to effect fractionation by using small supercritical fluid extraction apparatus or supercritical fluid chromatographs of the type which employs a small extraction vessel or separation column having an internal volume of 1 to 10 ml.

Figure 7:
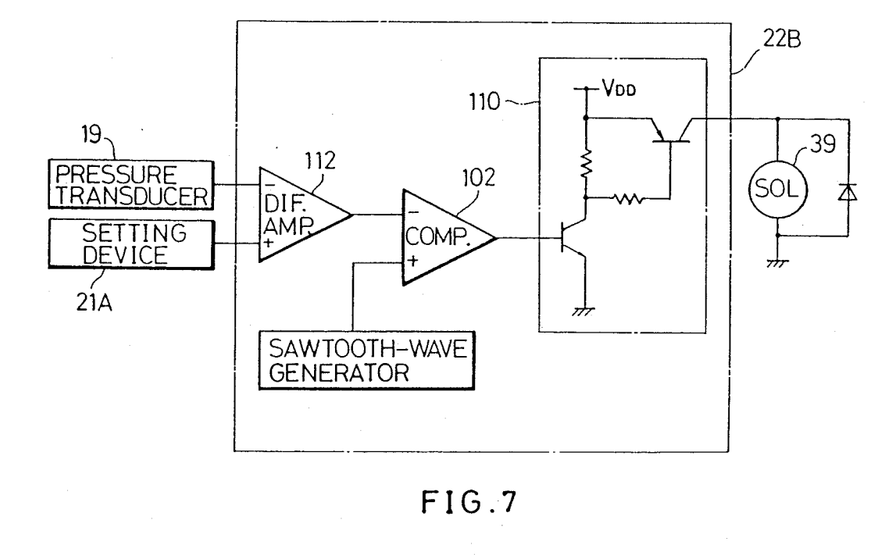
FIG. 7 is a circuit diagram of another example of the pressure adjusting device.

Another example of the pressure adjusting device 22 will be described below with reference to FIG. 7 in which this example is indicated generally at 22B.

The output voltage of the pressure transducer 19 is supplied to an inverting input terminal of a differential amplifier 112, and the output voltage of the programmed setting device 21A is supplied to a non-inverting input terminal of the differential amplifier 112, and the output voltage of the differential amplifier 112 in turn is supplied to a non-inverting input terminal of the comparator 102. The output voltage of a sawtoothwave generator 114 is supplied to a non-inverting input terminal of the comparator 102. The remaining portion of the example 22B is the same in construction as the previously-described example 22A shown in FIG. 6.

In the aforesaid construction, if the set pressure is raised, that is, if the output voltage of the differential amplifier 112 is raised, the ratio of an opening period $T_o$ to a closing period $T_c$ of the solenoid valve 20A, that is, the duty ratio of valve opening and valve closing becomes small and thus the pressure within the separation column 15 rises.

In the above-described example, the frequency of the opening and closing motions of the valve coincides with the frequency of the sawtooth wave. Therefore, the example is particularly effective when the frequency of small pressure variations in pressure control needs to be controlled within a predetermined range.

Figure 9:
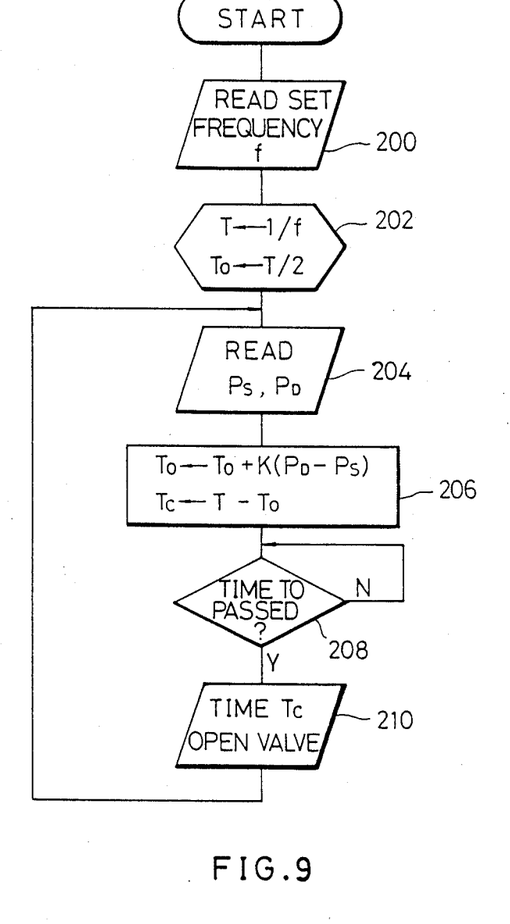
FIG. 9 is a flow chart illustrating one example of the software stored in a microcomputer which constitutes the pressure adjusting device.

Still another example of the pressure adjusting device 22 shown in FIG. 1 will be described below with reference to FIG. 9. In the following example, the pressure adjusting device 22 is constituted by a microcomputer. In addition, the pressure setting device 21 shown in FIG. 1 is capable of setting not only the level of pressure but also a frequency f of the opening and closing motions of the valve. FIG. 9 is a flow chart illustrating the software arrangement of the microcomputer.

Figure 8:
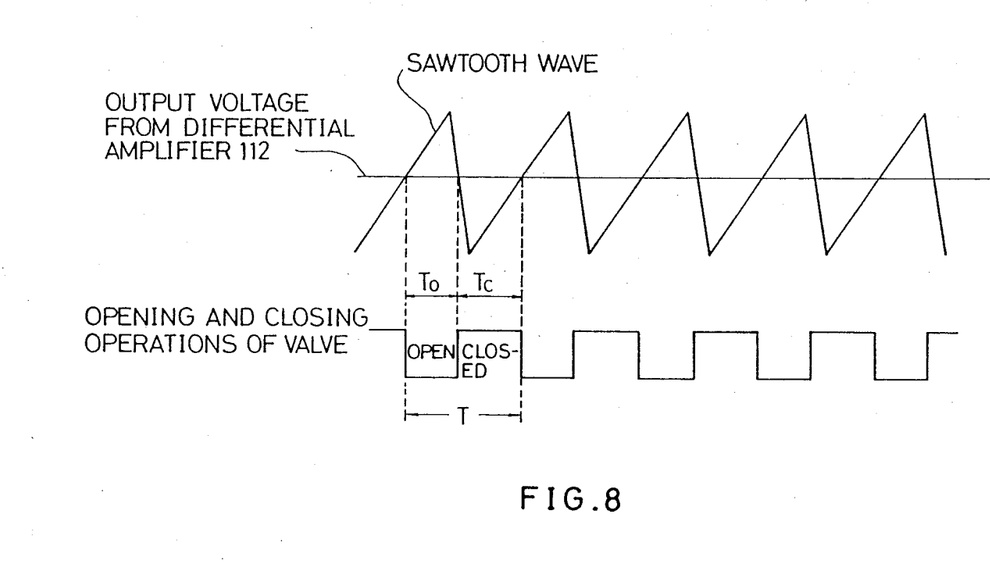
FIG. 8 is a timing chart illustrating the operation of the circuit shown in FIG. 7.

Referring to the flow chart of FIG. 9, reading of the set frequency f is effected in Step 200. In Step 202, a period T (see FIG. 8) which corresponds to one cycle of opening and closing of the valve is set to 1/f, and the valve-opening period $T_0$ in this period T is initialized and set to a half period.

In Step 204, the set pressure PS and the detection pressure $P_D$ are read. In Step 206, $K(P_D - P_S)$ is added to the valve-opening period $T_0$, and the result is set to a new valve opening period $T_o$ and $T - T_o$ is set to the valve closing period $T_c$ in one period. In Step 208, the process waits for the passage of the new valve opening period $T_o$, that is, the solenoid valve 20A is kept open for the time period $T_o$. In Step 210, the solenoid 39 is energized and the solenoid valve 20A is kept closed for the time period $T_c$. The process returns to Step 204 in which the above-described processing is repeated.

In this manner, the duty ratio of the valve opening period is adjusted, and feedback control is provided so that the detection pressure $P_D$ may be set to the desired pressure $P_S$.

Although, in the foregoing description, reference has been had to closed loop control for the purpose of illustration, it will be appreciated that open loop control may also be employed.

By way of example, the previous description is made with respect to an illustrative example in which the solenoid 39 is used as the drive source for the valve stem 30. However, it is of course possible to employ any type of element that can convert an electrical signal to a mechanical displacement. For example, a piezoelectric element may be used as the drive source, or the valve stem 30 itself may be constituted by a piezoelectric element.

Another embodiment of the apparatus for effecting extraction, chromatographic separation, and fractionation will be described below with reference to FIG. 10.

In this embodiment, an extraction fluid in the mobile phase is independent of an elution fluid in the same phase.

More specifically, as illustrated, constituent elements 301 to 305, 14 and 308 which correspond to the constituent elements 1 to 6 and 8, respectively, are connected along the flow passage between the pressure control valve 11 and the separation column 15, and the arrangement of the former constituent elements is substantially the same as that of the latter constituent elements. However, a port E of the six-way valve 303 is connected to an outlet of the pressure control valve 11, and a port B of the six-way valve 303 is connected to an inlet of the separation column 15. Also, while the cylinder 1 is charged with a liquefied gas as the extraction fluid, a cylinder 301 is charged with a liquefied gas as the elution fluid. The constituent element 6 serves as an extraction vessel, and the constituent element 14 serves as an adsorption column.

In addition, unlike the embodiment shown in FIG. 1, the thermostatic chamber 16 contains the six-way valve 303 as well as the adsorption column 14 and the separation column 15.

In respect of the remaining portion, this embodiment is identical to the embodiment shown in FIG. 1.

The operation of this embodiment having the above-described arrangement is described below with illustrative reference to a case in which a supercritical fluid is employed.

First of all, extraction and cleaning of a chromatograph, which will be described below, are performed as necessity demands.

A sample is placed into the extraction vessel 6, and the temperatures within the thermostatic chambers 7 and 16 are held at temperatures not lower than a critical temperature. The set pressures of the back-pressure regulators 9 and 18 are set to a level not lower than a critical pressure. In addition, flow passages A-B, C-D, and E-F (shown by dashed lines) of the six-way valve 303 are opened, and the flow passages B-C, D-E, and F-A (shown by solid lines) of the six-way valve 3 are opened. The valves 8 and 308 are opened.

In this state, the liquefied gas and the modifier solvent both of which are used for extraction are delivered from the cylinder 1 and the storage tank 4, respectively. In consequence, in the same manner as that of the previously-described embodiment, the liquefied gas is converted to a supercritical fluid in the extraction vessel 6. The supercritical fluid is gasified downstream of the pressure control valve 11, and the resultant extract is adsorbed by the adsorbent packed in the adsorption column 14. After completion of the extraction, the gas is discharged from the valve 308.

Simultaneously with the aforesaid operation, the liquefied gas and the modifier solvent, both of which are used for elution, are delivered from the cylinder 301 and the storage tank 304, respectively. In consequence, in the same manner as that of the previously-described embodiment, the flow passages in the chromatograph are cleaned.

Then, the following chromatographic separation and fractionation is carried out.

The motions of the pumps 2 and 5 are stopped, and the six-way valve 3 is switched to open the flow passages A-B, C-D, and E-F shown by the dashed lines. Thus, the gas filled in the extraction vessel 6 is discharged through the valve 8.

Then, the six-way valve 303 is switched to open the flow passages B-C, D-E, and F-A shown by the solid lines. Thus, the liquefied gas and the modifier solvent, both of which are used for elution are delivered, respectively, from the cylinder 301 and the storage tank 304 to the adsorption column 14. In consequence, separation and fractionation are effected in a similar manner to that of the previously-described embodiment.

It is to be noted that, the operation of effecting cleaning, extraction, or chromatographic separation and fractionation by using a liquefied gas in place of such a supercritical fluid is the same as the operation described previously in conjunction with the previously-described embodiment shown in FIG. 1.

Figure 10:
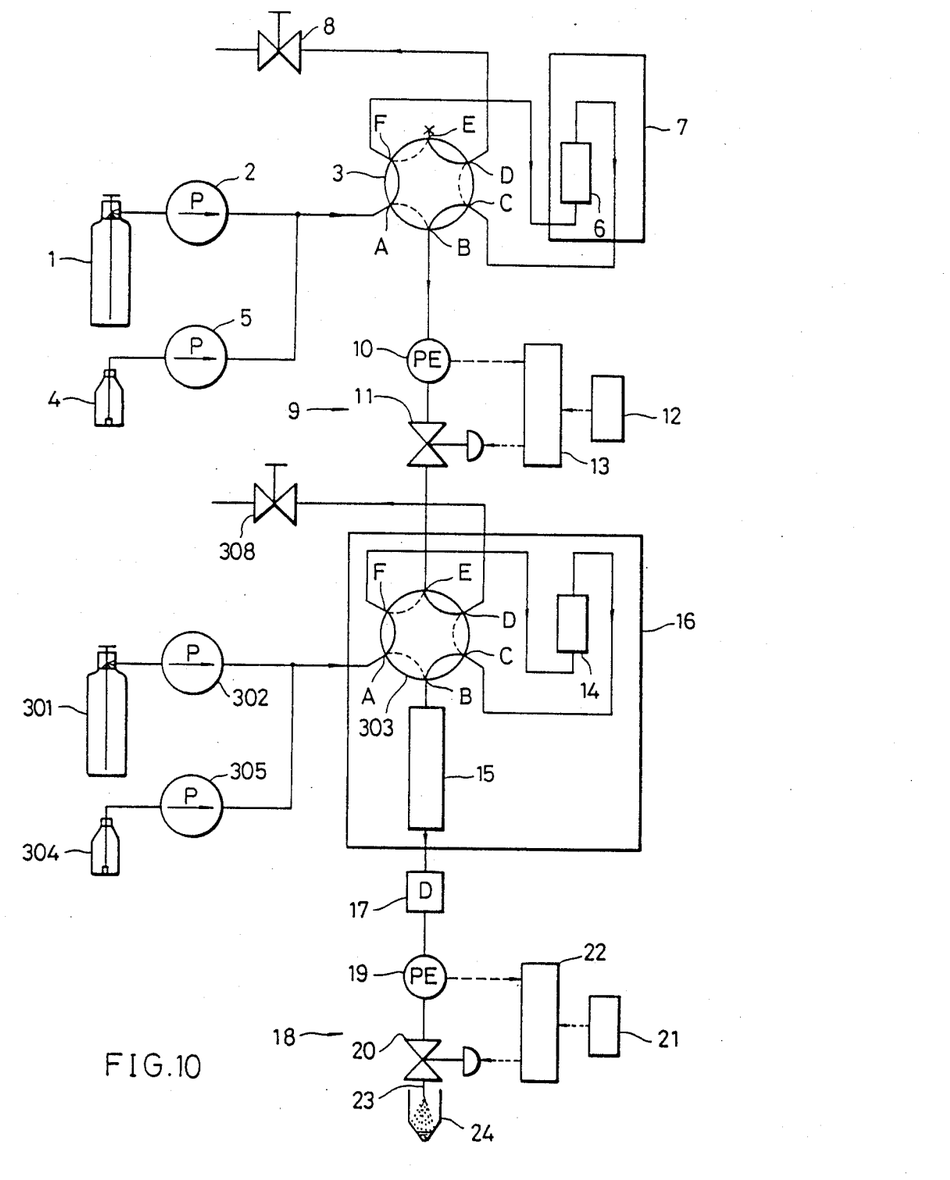
FIG. 10 is a circuit diagram illustrating an apparatus for effecting extraction, chromatographic separation, and fractionation in accordance with another embodiment of the present invention

In the embodiment shown in FIG. 10, since it is possible to effect extraction and cleaning at the same time, the period required for the entire processing can be greatly reduced.

Since the extraction fluid is separated from the elution fluid, optimum extraction and separation can be achieved without the need to replace the cylinder 1 and the storage tank 4 prior to chromatographic separation and fractionation.

In addition, it is possible to perform preliminary extraction and cleaning in a state wherein the flow passages B-C, D-E, and F-A (shown by the solid lines) of the six-way valves 3 and 303 are opened. More specifically, prior to the extraction of a desired extract, a non-desired substance, for example, a flavor, which is extracted under temperature and pressure conditions which differ from those of the desired extract, can be discharged through the valve 308 while being made to bypass the adsorption column 14. In this case, it is possible to clean not only the interior of the separation column 15 and also that of the adsorption column 14 at the same time. It is also possible to separate the desired extract at a high concentration by switching the six-way valve 303 after completion of the preliminary extraction.

Although the embodiment of FIG. 10 is more complicated in construction than the embodiment of FIG. 1, the number of six-way valves used is two. Accordingly, the embodiment of FIG. 10 is simpler in construction and operation than the prior art apparatus.

If a storage tank charged with an ordinary elution liquid is used in place of the cylinder 301, a high-performance liquid chromatographic separation can be effected.

It will be appreciated that the present invention embraces various modification and alternatives in addition to the embodiments which are described previously for the purpose of illustration only.

(1) Modified Forms of Apparatus for Effecting Extraction, Chromatographic Separation, and Fractionation The modifier solvent need not necessarily be used since extraction and chromatographic separation may be effected with a supercritical fluid only as occasion demands.

In place of the six-way valve, another type of valve may be employed to switch its flow passages in the same manner as described previously.

Both the adsorption column 14 and the separation column 15 may be constituted by a single container.

The detector 17 may be disposed between the pressure transducer 19 and the pressure control valve 20.

The detector 17 may not be disposed on the flow passage. Instead, after elutes have been fractionated into the collection reservoir 24 at predetermined time intervals, on-line or off-line analysis of the collected elutes may be performed by using a detector.

As one constituent element of second back-pressure regulating means which is set forth in the appended claims a branch pipe may be provided at an intermediate portion of the pipe in FIG. 1 which connects the adsorption column 14 and the separation column 15. During extraction, the branch pipe may be adapted to be opened so as to reduce the level of pressure.

The back-pressure regulating means may be constituted by a plurality of resistance pipes each having a different diameter and a valve disposed in each of the resistance pipes for opening and closing the flow passage thereof. A pressure transducer may be used to detect back pressure, thereby controlling the back pressure by utilizing a combination of the opened and closed states of all the valves.

"Predetermined values" relative to temperature and pressure which are set forth in the appended claims may vary within a predetermined range as in the case of ON-OFF control. Alternatively, the "predetermined values" may be varied with time through programmed setting.

In addition, the thermostatic chamber 7 serving as first thermostatic means and the thermostatic chamber 16 serving as second thermostatic means may be integral with each other. The second thermostatic means may be separately provided for accommodating each of the adsorption column and the separation column.

(2) Modified Forms of Pressure Control Apparatus

In the previous descriptions of the embodiments, closed-loop control is referred to for the purpose of illustration. The present invention is of course applicable to open-loop control.

Although the drive device for the valve stem 30 is constituted by the solenoid 39, the drive device in the present invention is not confined solely to such a solenoid, and any type of drive source capable of converting an electrical signal to a mechanical displacement may be employed. For example, a piezoelectric element may be used as such a drive source, or the valve stem itself may be constituted by a piezoelectric element.

The valve may be of any type that is capable of opening and closing the flow passage between its inlet and outlet. Therefore, the type of valve is not limited to that having a valve stem capable of moving back and forth along the axis thereof. For example, a slide spool type or rotary spool type of valve may also be employed.

In addition, applications of the pressure control apparatus of the present invention are not limited to the fields of supercritical fluid extraction apparatus or supercritical fluid chromatographs. For example, the present pressure control apparatus are applicable to research on the balanced states of fluids in a gaseous or liquid phase. In addition, if the pressure control apparatus of the present invention of various sizes are prepared, they can be applied to chemical plants or any other field that requires accurate control of pressure.

In the above description, the fluid flowing in the valve is a supercritical fluid or liquid, but a gas may be used as the fluid. However, since the response speeds of liquids are commonly higher than those of gases, further accurate control can be provided over pressure by using liquids.

In the aforesaid embodiments, the above description is made with respect to a back pressure regulator which is a pressure control apparatus including the pressure transducers 10 and 19 which are disposed upstream of the pressure control valves 11 and 17, respectively. However, if the pressure transducers are disposed downstream of the pressure control valves, the pressure control apparatus is operable as a reduced-pressure control apparatus.

Accordingly, the present invention is intended to cover all alternatives, modifications and equivalents as may be included within the spirit and scope of the invention as defined by the appended claims.

We claim:

1. A back-pressure control apparatus in an apparatus for extracting a soluble substance or separating said soluble substance into its components comprising
   an electrically operable valve having small dead volume and operable between providing a fully open flow passage and a fully closed flow passage;
   said valve located downstream of the extraction or separating apparatus;
   a fluid passing through said valve being in either a supercritical state or liquefied gas state;
   a pressure transducer for detecting a pressure $P_D$ at a position upstream of said valve;
   means for setting a predetermined pressure $P_S$ having a valve greater than the critical pressure of said fluid;
   and means for controlling operation of said valve between said open flow passage and said closed flow passage by controlling the opening and closing cyclically at a changing frequency in response to detection of said pressure $P_D$ so as to limit change of said pressure $P_D$ towards said pressure $P_S$.

2. The apparatus according to claim 1, wherein means for controlling operation is arranged to close said valve when $P_D < P_S$ and to open said valve when $P_D > P_S$.

3. The apparatus according to claim 1, wherein said valve further includes a valve stem capable of moving back and forth along the axis thereof to open and close said flow passage.

4. The apparatus according to claim 3, wherein said valve stem is driven by an electromagnetic force.

5. The apparatus according to claim 3, wherein said valve stem is driven by the application of a voltage to a piezoelectric element.

6. A back-pressure control apparatus in an apparatus for extracting a soluble substance or separating said soluble substance into its components comprising
   an electrically operable valve having small dead volume and operable between providing a fully open flow passage and a fully closed flow passage;
   said valve located downstream of the extraction or separating apparatus;
   a fluid passing through said valve being in either a supercritical state or liquefied gas state;
   and means for controlling operation of said valve between said open flow passage and said closed flow passage by controlling the opening and closing cyclically at a changing frequency.

7. A back-pressure control apparatus in an apparatus for extracting a soluble substance or separating said soluble substance into its components comprising
   an electrically operable valve having small dead volume and operable between providing a fully open flow passage and a fully closed flow passage;
   said valve located downstream of the extraction or separating apparatus;
   a fluid passing through said valve being in either a supercritical state or liquefied gas state;
   and means for controlling operation of said valve between said open flow passage and aid closed flow passage by controlling the opening and closing cyclically at a changing duty ratio.

8. A back-pressure control apparatus in an apparatus for extracting a soluble substance or separating said soluble substance into its components comprising
   an electrically operable valve having small dead volume and operable between providing a fully open flow passage and a fully closed flow passage;

said valve located downstream of the extraction or separating apparatus;

a fluid passing through said valve being in either a supercritical state or liquefied gas state;

a pressure transducer for detecting a pressure $P_D$ at a position upstream of said valve;

means for setting a predetermined pressure $P_S$ having a valve greater than the critical pressure of said fluid;

and means for controlling operation of said valve between said open flow passage and said closed flow passage by controlling the opening and closing cyclically at a changing duty ratio in response to detection of said pressure $P_D$ so as to limit change of said pressure $P_D$ towards said pressure $P_S$.

* * * * *